United States Patent
Cao et al.

(10) Patent No.: US 11,442,183 B2
(45) Date of Patent: Sep. 13, 2022

(54) SEMICONDUCTOR RADIATION DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/365,421

(22) Filed: Jul. 1, 2021

(65) Prior Publication Data

US 2021/0325552 A1 Oct. 21, 2021

Related U.S. Application Data

(63) Continuation of application No. PCT/CN2019/071117, filed on Jan. 10, 2019.

(51) Int. Cl.
*G01T 1/24* (2006.01)
*A61B 6/03* (2006.01)
*A61B 6/00* (2006.01)

(52) U.S. Cl.
CPC ............ *G01T 1/24* (2013.01); *A61B 6/032* (2013.01); *A61B 6/4208* (2013.01)

(58) Field of Classification Search
CPC .......... G01T 1/24; A61B 6/032; A61B 6/4208
See application file for complete search history.

(56) References Cited

U.S. PATENT DOCUMENTS

| | | | |
|---|---|---|---|
| 6,204,087 B1 * | 3/2001 | Parker | H01L 27/1446 257/E27.129 |
| 6,943,409 B1 * | 9/2005 | Cheng | B82Y 20/00 257/330 |
| 2010/0020733 A1 | 1/2010 | Hartman | |

(Continued)

FOREIGN PATENT DOCUMENTS

| CN | 107533145 A | 1/2018 |
|---|---|---|
| WO | 2016163347 A1 | 10/2016 |

OTHER PUBLICATIONS

Koybasi, Ozhan, et al. "Electrical Characterization and Preliminary Beam Test Results of 3D Silicon CMS Pixel Detectors." IEEE Transaction on Nuclear Science 58.3 (2011): 1315-1323.

(Continued)

*Primary Examiner* — Hugh Maupin
(74) *Attorney, Agent, or Firm* — IPro, PLLC; Qian Gu

(57) ABSTRACT

Disclosed herein is a radiation detector comprising: an electronics layer comprising a first set of electric contacts and a second set of electric contacts; a radiation absorption layer configured to absorb radiation; a first set of electrodes and a second set of electrodes, wherein the first set of electrodes and the second set of electrodes are interdigitated and extend into the radiation absorption layer in a direction of thickness thereof; wherein the electronics layer and the radiation absorption layer are bonded such that the first set of electrodes are electrically connected to the first set of electric contacts and the second set of electrodes are electrically connected to the second set of electric contacts.

45 Claims, 17 Drawing Sheets

(56) References Cited

U.S. PATENT DOCUMENTS

2010/0155615 A1* 6/2010 Whitehead ................ G01T 1/26
 250/370.14
2015/0323679 A1 11/2015 Yang et al.
2021/0223420 A1* 7/2021 Ullberg .................. G01T 1/247

OTHER PUBLICATIONS

Koybasi, Ozhan, et al. "Design, simulation, fabrication, and preliminary tests of 3D CMS pixel detectors for the Super-LHC." IEEE Transaction on Nuclear Science 57.5 (2010): 2897-2905.

* cited by examiner

SEMICONDUCTOR RADIATION DETECTOR

BACKGROUND

Radiation detectors may be devices used to measure the flux, spatial distribution, spectrum or other properties of radiations.

Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, Radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a particle of radiation is absorbed in the semiconductor layer, multiple charge carriers (e.g., electrons and holes) are generated and swept under an electric field towards electric contacts on the semiconductor layer. Cumbersome heat management required in currently available semiconductor radiation detectors (e.g., Medipix) can make a detector with a large area and a large number of pixels difficult or impossible to produce.

SUMMARY

Disclosed herein is a radiation detector comprising: an electronics layer comprising a first set of electric contacts and a second set of electric contacts; a radiation absorption layer configured to absorb radiation; a first set of electrodes and a second set of electrodes, wherein the first set of electrodes and the second set of electrodes are interdigitated and extend into the radiation absorption layer in a direction of thickness thereof; wherein the electronics layer and the radiation absorption layer are bonded such that the first set of electrodes are electrically connected to the first set of electric contacts and the second set of electrodes are electrically connected to the second set of electric contacts.

According to an embodiment, the radiation absorption layer comprises GaAs, CdTe, CZT, or a combination thereof.

According to an embodiment, the first set of electrodes and the second set of electrodes comprise a metal or a semiconductor.

According to an embodiment, the first set of electrodes and the second set of electrodes are configured to be differentially biased.

According to an embodiment, a distance between one of the first set of electrodes to its nearest neighbor of the second set of electrodes does not exceed $2\lambda$, wherein $\lambda$ is the mean free path of charge carriers in the radiation absorption layer.

According to an embodiment, the second set of electrodes are cylindrical in shape.

According to an embodiment, the second set of electrodes are prismatic in shape.

According to an embodiment, the first set of electrodes comprises a grid.

According to an embodiment, the second set of electrodes are discrete.

According to an embodiment, the first set of electrodes and the second set of electrodes are coextensive in the direction of thickness.

According to an embodiment, the radiation detector further comprises an insulating layer at a surface of the radiation absorption layer distal from the electronics layer; wherein the first set of electrodes and the second set of electrodes are attached to the insulating layer.

According to an embodiment, the radiation absorption layer comprises a polycrystalline semiconductor.

According to an embodiment, the electronics layer is configured to bias the first set of electrodes and the second set of electrodes to different electric voltages through the first set of electric contacts and the second set of electric contacts.

According to an embodiment, the radiation is X-ray.

According to an embodiment, the electronics layer comprises: a first voltage comparator configured to compare a voltage of an electric contact of the second set of electric contacts to a first threshold; a second voltage comparator configured to compare the voltage to a second threshold; a counter configured to register a number of particles of radiation received by the radiation absorption layer; a controller, wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, upon determination by the second voltage comparator that an absolute value of the voltage equals or exceeds an absolute value of the second threshold.

According to an embodiment, the radiation detector further comprises an integrator electrically connected to the electric contact, wherein the integrator is configured to collect charge carriers from the electric contact.

According to an embodiment, the controller is configured to activate the second voltage comparator at a beginning or expiration of the time delay.

According to an embodiment, the controller is configured to connect the electric contact to an electrical ground.

According to an embodiment, a rate of change of the voltage is substantially zero at expiration of the time delay.

Disclosed herein is a method comprising obtaining a substrate with an insulating layer and a semiconductor layer attached to the insulating layer; forming a first set of electrodes and a second set of electrodes from the semiconductor layer by etching the semiconductor layer through its entire thickness; introducing semiconductor particles among the first set of electrodes and the second set of electrodes; bonding the semiconductor layer with an electronics layer comprising a first set of electric contacts and a second set of electric contacts, such that the first set of electrodes are electrically connected to the first set of electric contacts and the second set of electrodes are electrically connected to the second set of electric contacts.

According to an embodiment, the semiconductor particles comprise GaAs, CdTe, CZT, or a combination thereof.

According to an embodiment, introducing the semiconductor particles among the first set of electrodes and the second set of electrodes comprises fusing the semiconductor particles.

According to an embodiment, the first set of electrodes and the second set of electrodes are configured to be differentially biased.

According to an embodiment, a distance between one of the first set of electrodes to its nearest neighbor of the second set of electrodes does not exceed 2λ, wherein λ is the mean free path of charge carriers across the semiconductor particles.

According to an embodiment, the second set of electrodes are cylindrical in shape.

According to an embodiment, the second set of electrodes are prismatic in shape.

According to an embodiment, the first set of electrodes comprises a grid.

According to an embodiment, the second set of electrodes are discrete.

According to an embodiment, the electronics layer is configured to bias the first set of electrodes and the second set of electrodes to different electric voltages through the first set of electric contacts and the second set of electric contacts.

According to an embodiment, the method further comprises removing the insulating layer.

DETAILED DESCRIPTION

Figure 1A:
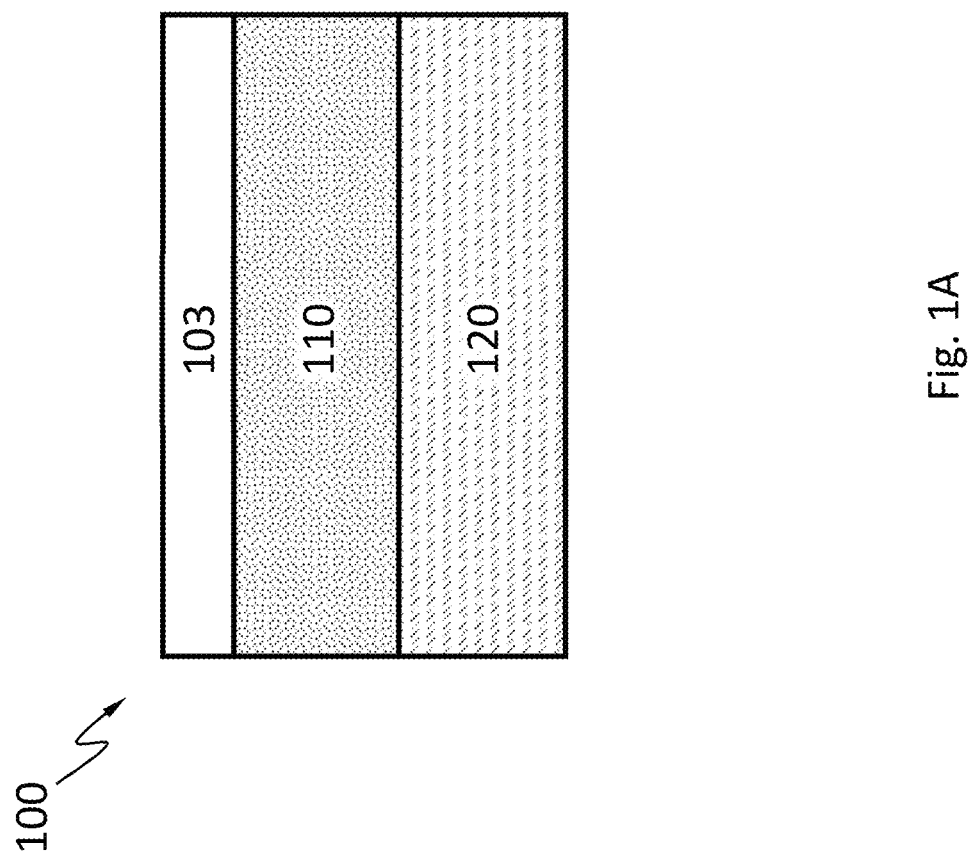
FIG. 1A schematically shows a cross-sectional view of a radiation detector, according to an embodiment.

FIG. 1A schematically shows a cross-sectional view of a radiation detector 100, according to an embodiment. The radiation detector 100 may include a radiation absorption layer 110 configured to absorb radiation and an electronics layer 120 (e.g., an ASIC) for processing or analyzing electrical signals incident radiation generates in the radiation absorption layer 110. In an embodiment, the radiation detector 100 does not comprise a scintillator. The radiation absorption layer 110 may include a polycrystalline semiconductor material such as, GaAs, CdTe, CdZnTe (CZT), or a combination thereof. The semiconductor may have a high mass attenuation coefficient for the radiation energy of interest. The radiation detector 100 may further comprise an insulating layer 103 at a surface of the radiation absorption layer 110 distal from the electronics layer 120. The radiation may be X-ray.

Figure 1B:
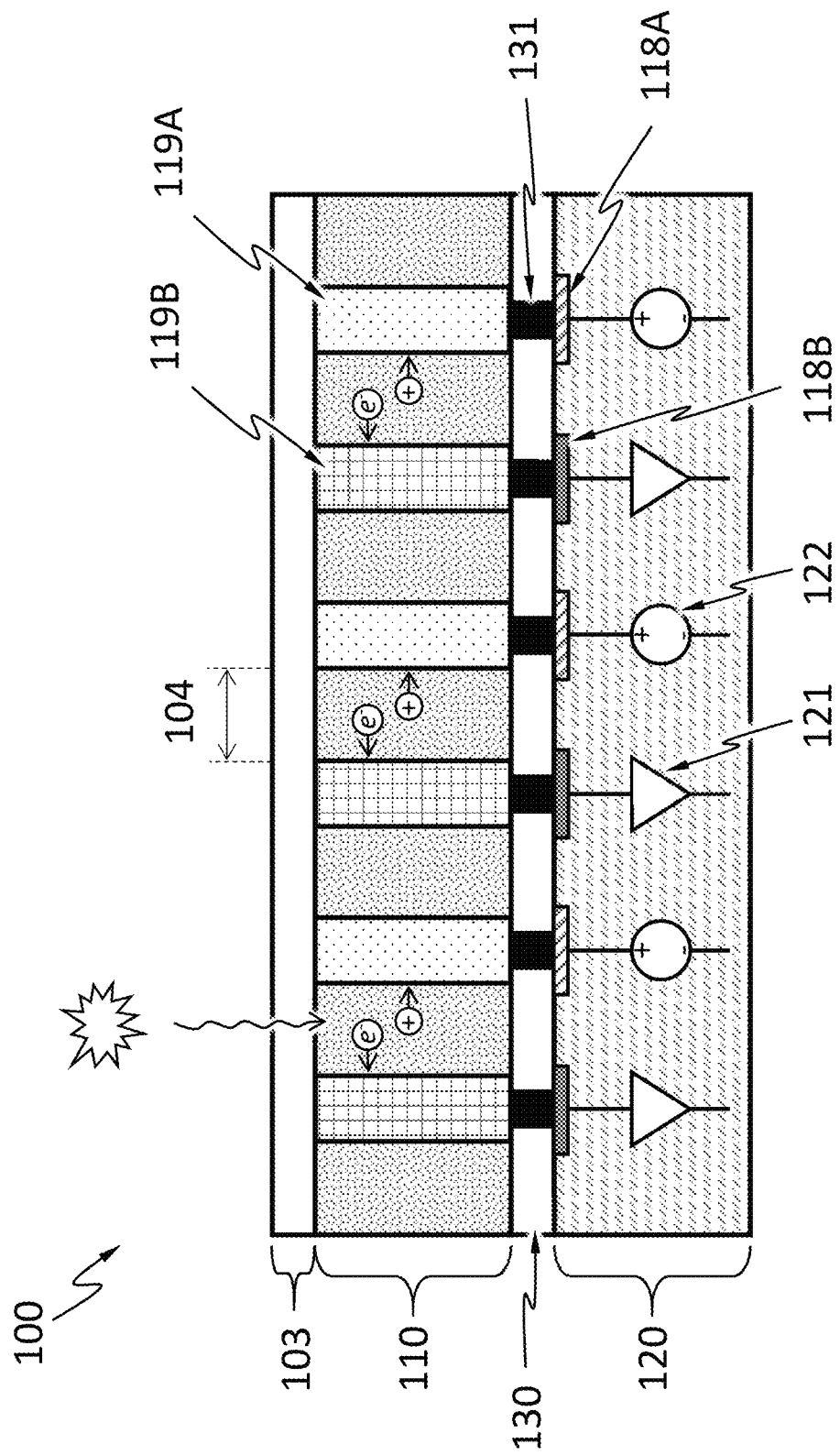
FIG. 1B schematically shows a detailed cross-sectional view of the radiation detector.

As shown in a detailed cross-sectional view of the radiation detector 100 in FIG. 1B, according to an embodiment, the radiation detector 100 includes a first set of electrodes 119A and a second set of electrodes 119B that are interdigitated and extend into the radiation absorption layer 110 in a direction of thickness of the radiation absorption layer 110. The first set of electrodes 119A and the second set of electrodes 119B may comprise a metal or a semiconductor material. The first set of electrodes 119A and the second set of electrodes 119B may be coextensive in the direction of thickness of the radiation absorption layer 110. The first set of electrodes 119A and the second set of electrodes 119B may be attached to the insulating layer 103.

When a particle of radiation hits the radiation absorption layer 110, it may be absorbed by the radiation absorption layer 110 and the radiation absorption layer 110 may generate one or more charge carriers by a number of mechanisms, as shown in FIG. 1B. A particle of radiation may generate 10 to 100000 charge carriers. The charge carriers may drift to the first set of electrodes 119A and the second set of electrodes 119B under an electric field. The electric field may be established by differentially biasing the first set of electrodes 119A and the second set of electrodes 119B. According to an embodiment, a distance (e.g., 104 in FIG. 1B) between one electrode of the first set of electrodes 119A to its nearest neighbor of the second set of electrodes 119B does not exceed 2λ, wherein λ is the mean free path of charge carriers in the radiation absorption layer 110.

Figure 1D:
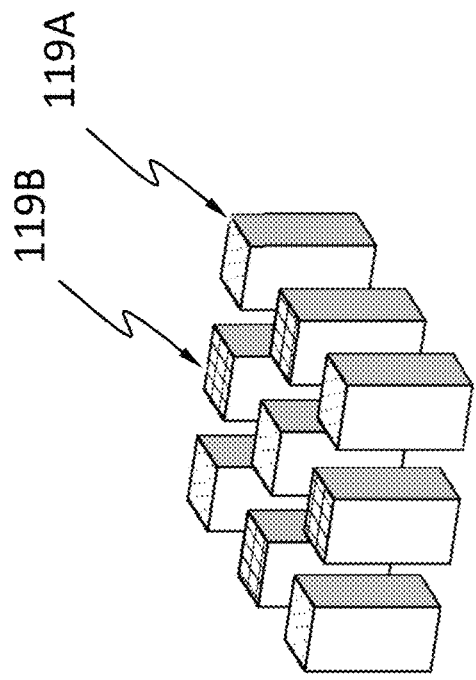
FIG. 1C-FIG. 1E each schematically show a suitable configuration of a first set of electrodes and a second set of electrodes of the radiation detector, according to an embodiment.
Figure 1C:
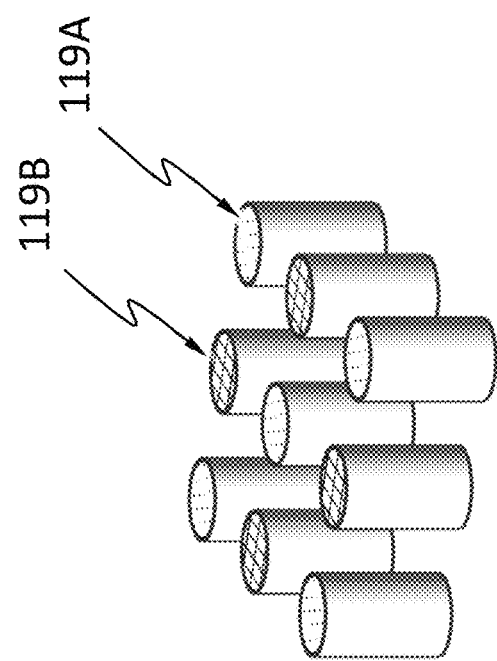
Figure 1E:
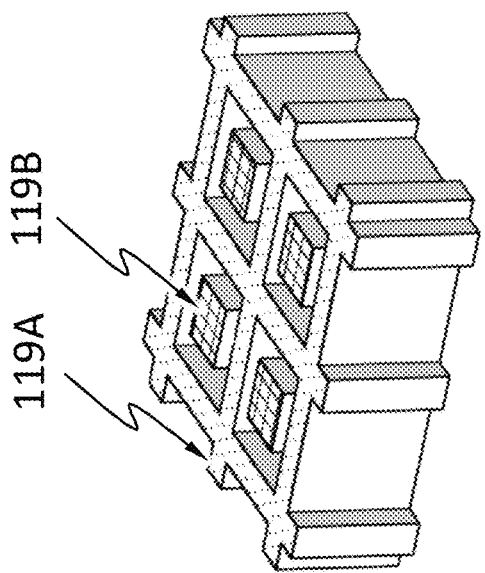

The first set of electrodes 119A and the second set of electrodes 119B may have any suitable size and shapes, as shown in the examples of FIG. 1C-FIG. 1E. According to an embodiment (e.g., in FIG. 1C), at least some of the second set of electrodes are discrete and cylindrical in shape. According to an embodiment (e.g., in FIG. 1D), at least some of the second set of electrodes are discrete and prismatic in shape. According to an embodiment (e.g., in FIG. 1E), the first set of electrodes comprises a grid and at least some of the second set of electrodes are discrete.

The electronics layer 120 may include an electronic system 121 suitable for processing or interpreting signals generated from radiation incident on the radiation absorption layer 110. The electronic system 121 may include an analog circuitry such as a filter network, amplifiers, integrators, and comparators, or a digital circuitry such as a microprocessor, and memory. The electronic system 121 may be electrically bonded to the radiation absorption layer 110 by vias 131. Space among the vias may be filled with a filler material 130, which may increase the mechanical stability of the connection of the electronics layer 120 to the radiation absorption layer 110. Other bonding techniques are possible to connect the electronic system 121 to the radiation absorption layer 110 without using vias.

The electronics layer 120 has a first set of electric contacts 118A and a second set of electric contacts 118B. After the electronics layer 120 and the radiation absorption layer 110 are bonded, the first set of electrodes 119A are electrically connected to the first set of electric contacts 118A (by via 131) and the second set of electrodes 119B are electrically connected to the second set of electric contacts 118B (e.g., by via 131). The electronics layer 120 may be configured to bias the first set of electrodes 119A and the second set of electrodes 119B to different electric voltages through the first set of electric contacts 118A and the second set of electric contacts 118B, respectively. For example, one or more voltage sources 122 may supply a non-zero voltage to the first set of electric contacts 118A and the second set of electric contacts 118B may be connected to the virtual ground of an amplifier in the electronic system 121.

Figure 2A:
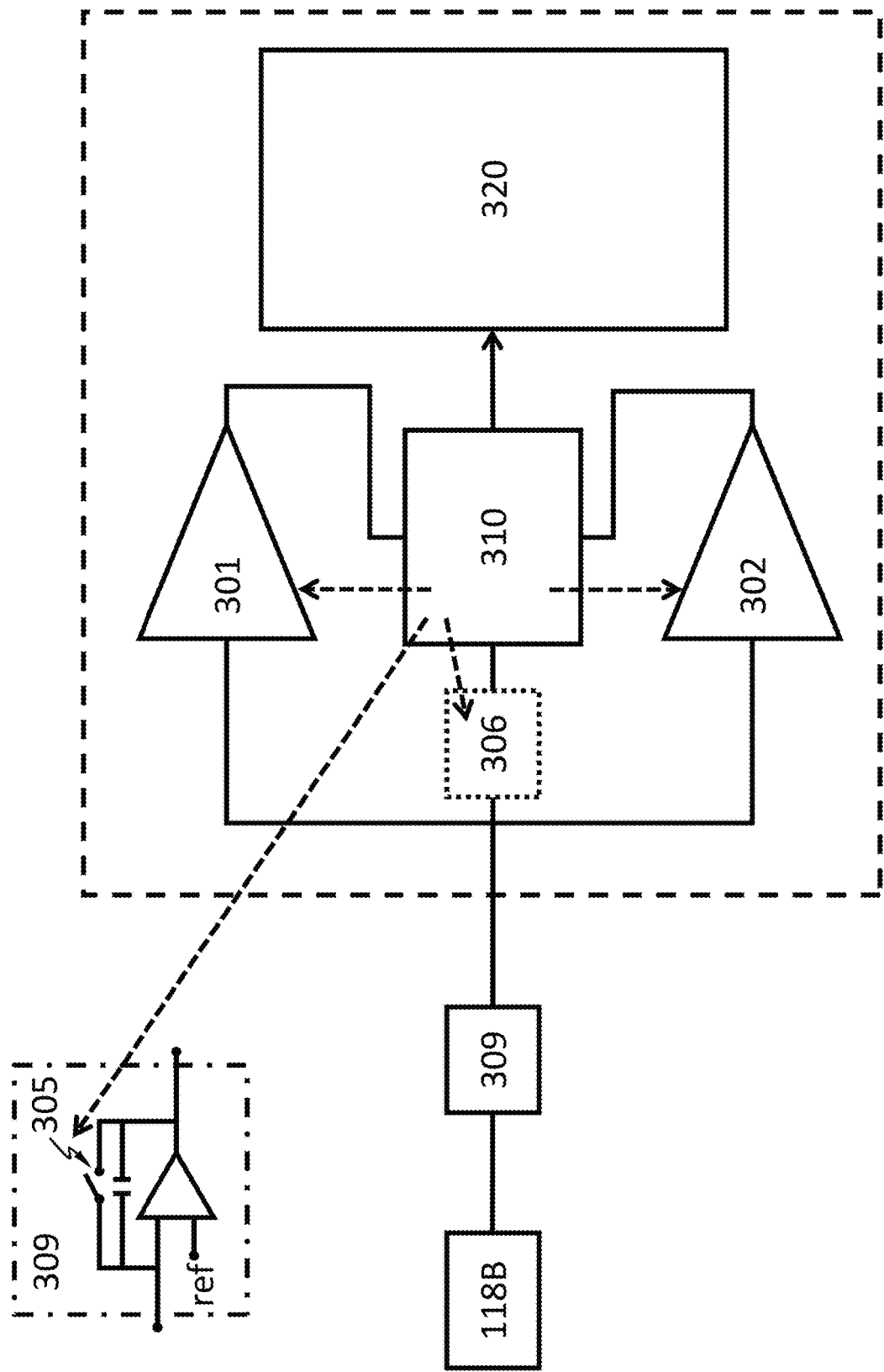
FIG. 2A and FIG. 2B each schematically show a component diagram of the electronic system of the detector, according to an embodiment.
Figure 2B:
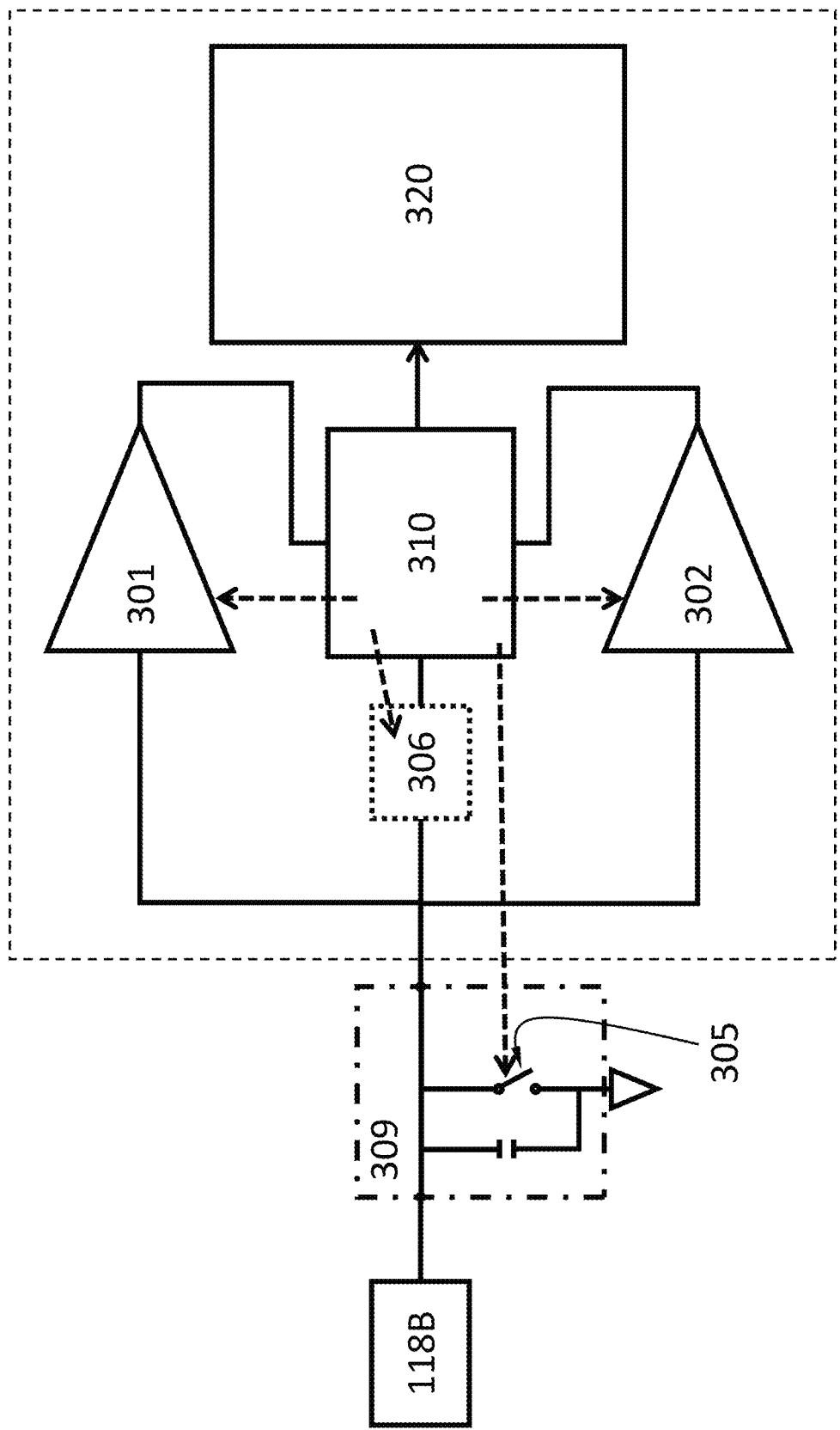

FIG. 2A and FIG. 2B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare a voltage of an electric contact of the second set of electric contacts 118B to a first threshold. The first voltage comparator 301 may be configured to monitor the voltage directly or calculate the voltage by integrating an electric current flowing through the electric contact over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator, which has the benefit of lower power consumption. The first threshold may be 5-10%, 10%-20%, 20-30%, 30-40% or 40-50% of the voltage a single pulse of visible light may generate on the electric contact. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the electric contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" Ix' of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident particle of radiation may generate on an electric contact of the second set of electric contact 118B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident particles of radiation. However, having a high speed is often at the cost of power consumption.

The counter 320 is configured to register at least a number of particles of radiation received by the radiation absorption layer 110 (e.g., particles of radiation that generate charge carriers collected by a certain subset of the first set of electrodes 119A and a certain subset of the second set of electrodes 119B). The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electric contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 118B to an electrical ground, so as to reset the voltage and discharge any charge carriers accumulated on the electric contact 118B. In an embodiment, the electric contact 118B is connected to an electrical ground after the expiration of the time delay. In an embodiment, the electric contact 118B is connected to an electrical ground for a finite reset time period. The controller 310 may connect the electric contact 118B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 118B, wherein the integrator is configured to collect charge carriers from the electric contact 118B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 118B accumulate on the capacitor over a period of time ("integration period"). After the integration period has expired, the capacitor voltage is sampled and then reset by a reset switch. The integrator 309 can include a capacitor directly connected to the electric contact 118B.

Figure 3:
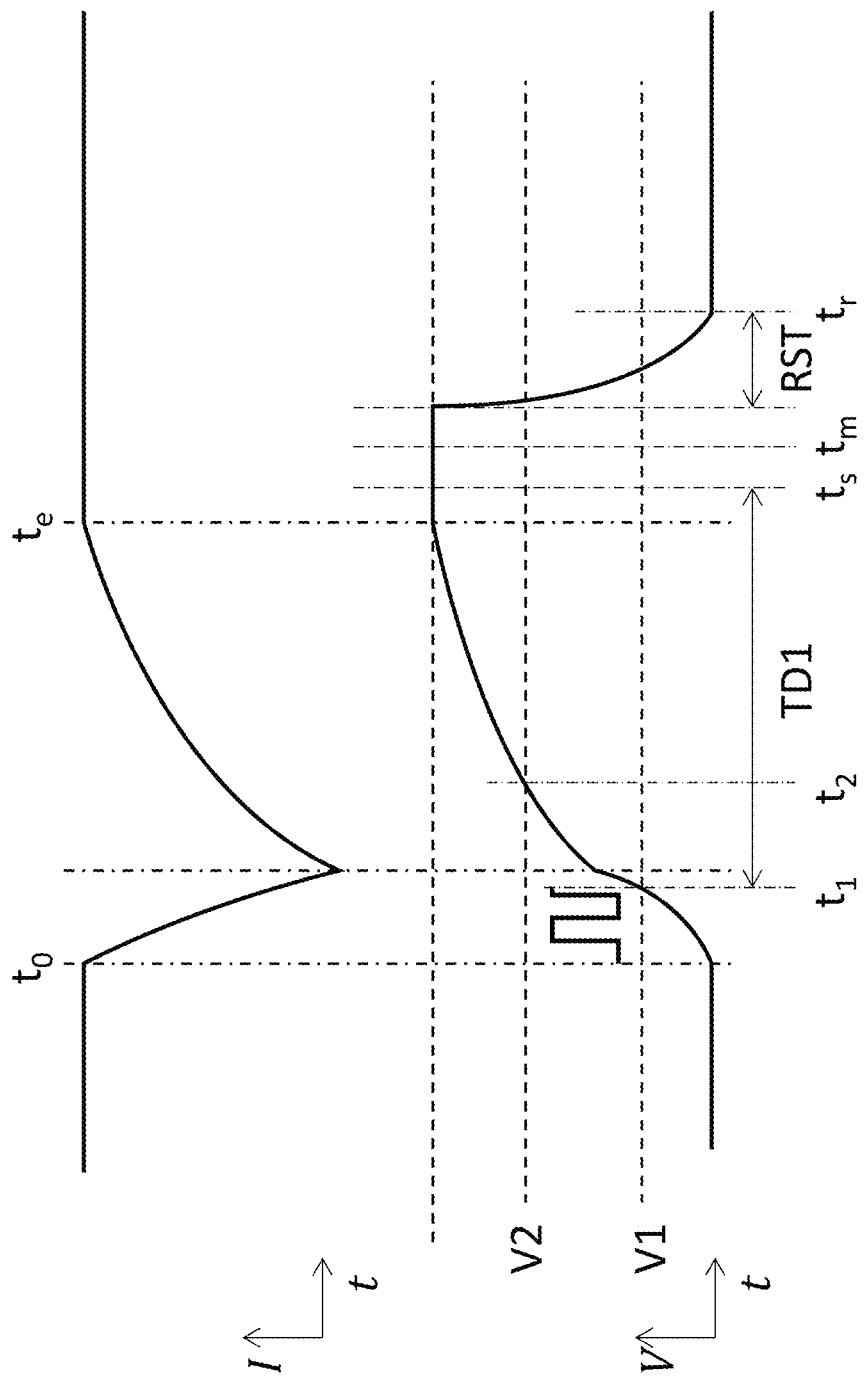
FIG. 3 schematically shows a temporal change of the electric current flowing through an electric contact (upper curve) caused by charge carriers generated by a pulse of visible light incident on a pixel associated with the electric contact, and a corresponding temporal change of the voltage of the electric contact (lower curve).

FIG. 3 schematically shows a temporal change of the electric current flowing through the electric contact 118B (upper curve) caused by charge carriers generated by a particle of radiation, and a corresponding temporal change of the voltage of the electric contact 118B (lower curve). The voltage may be an integral of the electric current with respect to time. At time $t_0$, the particle of radiation hits the radiation absorption layer 110, charge carriers start being generated in the radiation absorption layer 110, electric current starts to flow through the electric contact 118B, and the absolute value of the voltage of the electric contact 118B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 3, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 118B to an electric ground for a reset period RST to allow charge carriers accumulated on the electric contact 118B to flow to the ground and reset the voltage. After RST, the electronic system 121 is ready to detect another incident particle of radiation. If the first voltage comparator 301 has been deactivated, the controller 310 can activate it at any time before RST expires. If the controller 310 has been deactivated, it may be activated before RST expires.

Figure 4A:
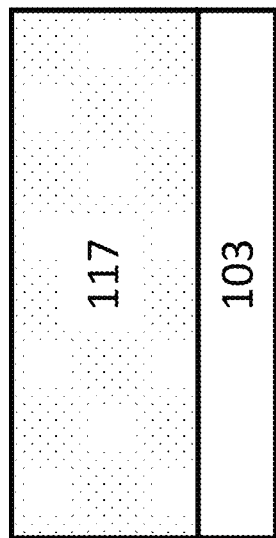
FIG. 4A-FIG. 4F schematically show a flowchart for a method of making the radiation detector, according to an embodiment.

FIG. 4A-FIG. 4F schematically shows a flowchart for a method of making the radiation detector 100, according to an embodiment. FIG. 4A schematically shows that the flow starts with a substrate with an insulating layer 103 and a semiconductor layer 117 attached to the insulating layer 103. In one example, the semiconductor layer 117 may be heavily doped silicon.

Figure 4B:
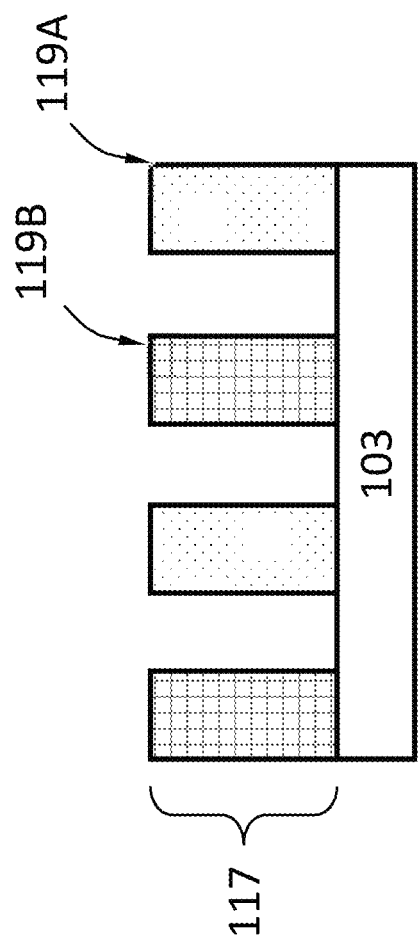

FIG. 4B schematically shows that the first set of electrodes 119A and the second set of electrodes 119B are formed by etching the semiconductor layer 117 through its entire thickness. As shown in the examples earlier, the first set of electrodes 119A may or may not have the same shapes or structures as the second set of electrodes 119B.

Figure 4C:
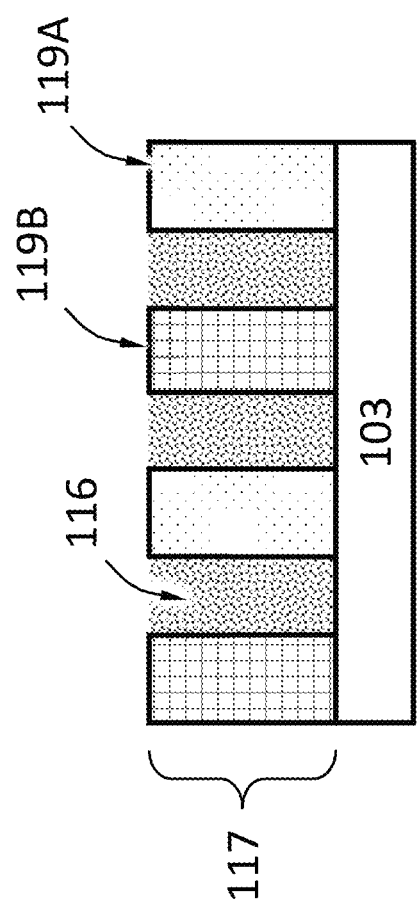

FIG. 4C schematically shows semiconductor particles 116 are introduced into spaces between the first set of electrodes 119A and the second set of electrodes 119B. For example, the spaces may be filled with a slurry containing the semiconductor particles 116 distributed in a fluid that will be later removed. The semiconductor particles 116 may comprise GaAs, CdTe, CZT, or a combination thereof. The semiconductor particles 116 may include other suitable semiconductors. In one example, the semiconductor particles 116 are fused. After fusion, at least some of the semiconductor particles 116 may become polycrystalline semiconductors. After fusion, there may still be void space among the semiconductor particles 116.

Figure 4D:
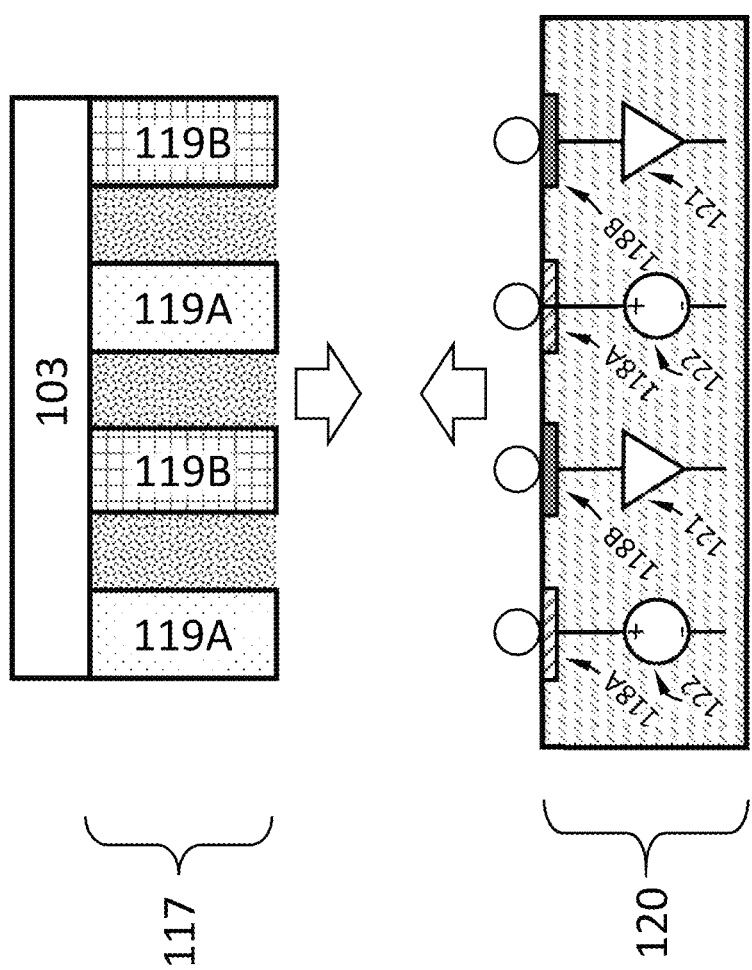
Figure 4E:
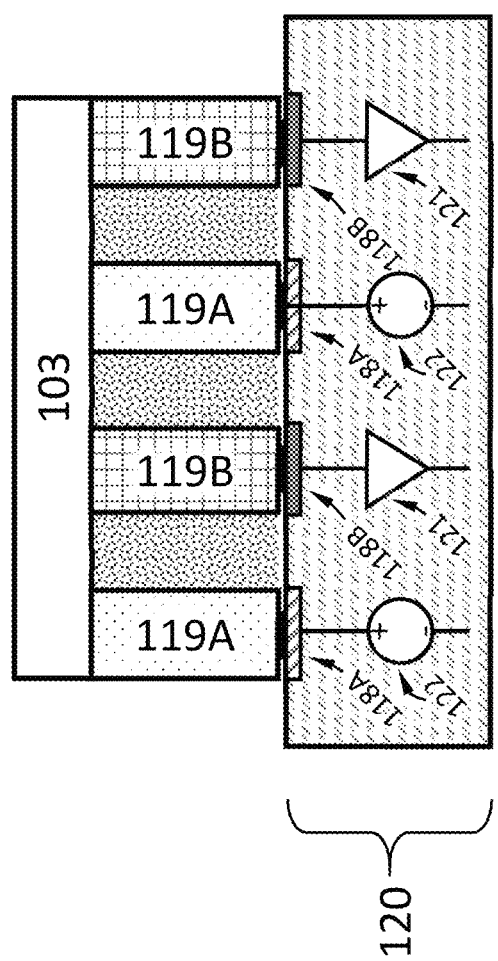

FIG. 4D schematically shows that the semiconductor layer 117, now containing the first set of electrodes 119A and the second set of electrodes 119B, is bonded to the electronics layer 120. FIG. 4E schematically shows that after bonding, the first set of electrodes 119A are electrically connected to the first set of electric contacts 118A and the second set of electrodes 119B are electrically connected to the second set of electric contacts 118B. More than one chip may be bonded to the same electronics layer 120, where each chip comprises the radiation absorption layer 110.

Figure 4F:
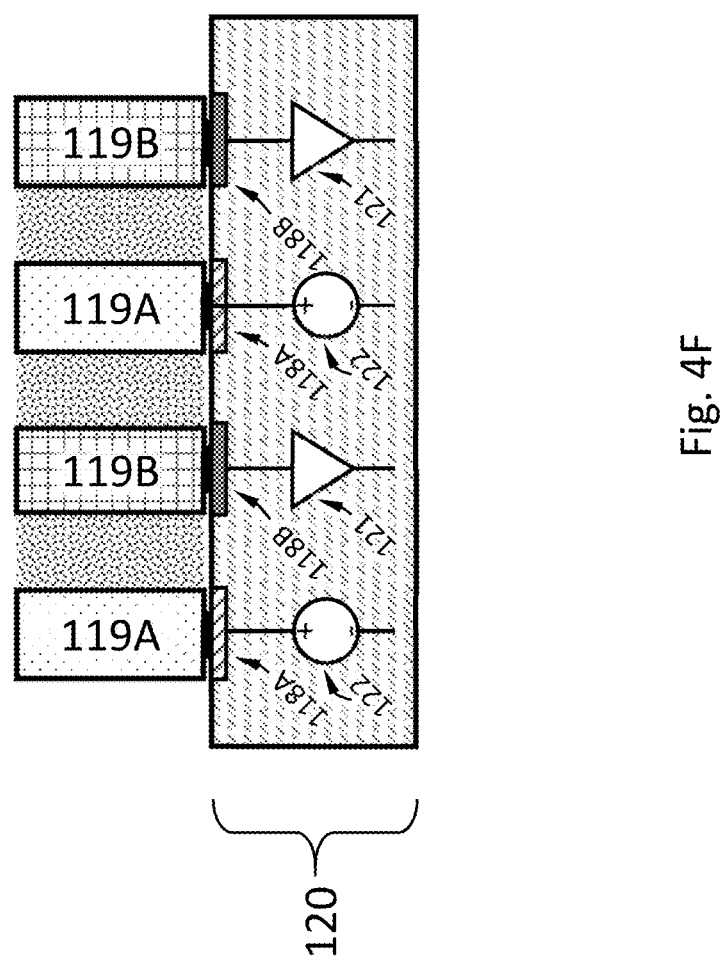

FIG. 4F schematically shows that the insulating layer 103 may be removed after bonding.

The radiation detector 100 described above may be used in various systems such as those provided below.

Figure 5:
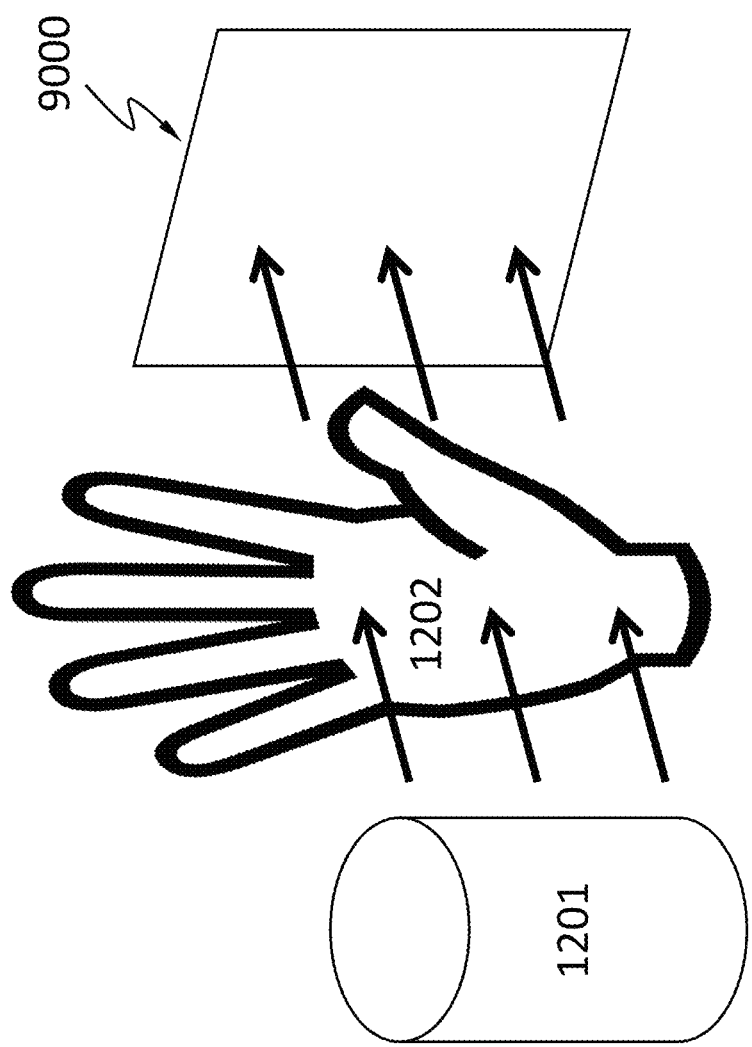
FIG. 5-FIG. 9 each schematically show a system comprising the radiation detector described herein.

FIG. 5 schematically shows a system 9000 comprising the radiation detector 100 as described herein. The system may be used for medical imaging such as chest radiation radiography, abdominal radiation radiography, etc. The system comprises a radiation source 1201. Radiation emitted from the radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the system 9000. The system 9000 forms an image by detecting the intensity distribution of the radiation.

Figure 6:
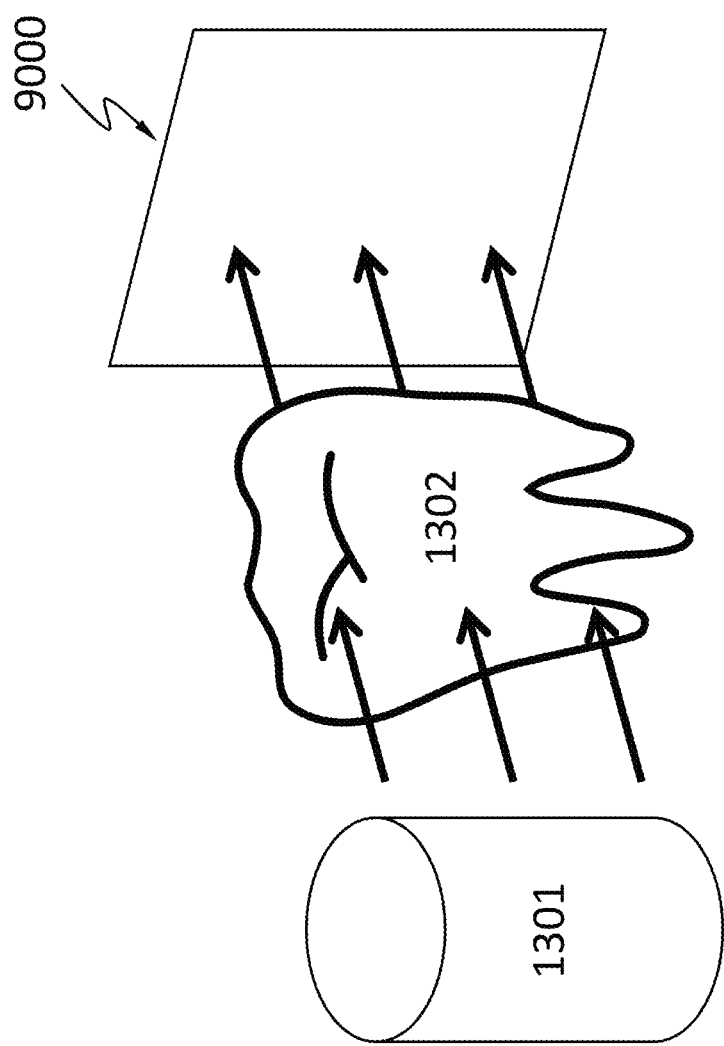

FIG. 6 schematically shows a system 9000 comprising the radiation detector 100 as described herein. The system may be used for medical imaging such as dental radiation radiography. The system comprises a radiation source 1301. Radiation emitted from the radiation source 1301 penetrates an object 1302 that is part of a mammal (e.g., human) mouth. The object 1302 may include a maxilla bone, a palate bone, a tooth, the mandible, or the tongue. The radiation is attenuated by different degrees by the different structures of the object 1302 and is projected to the system 9000. The system 9000 forms an image by detecting the intensity distribution of the radiation. Teeth absorb radiation more than dental caries, infections, periodontal ligament. The dosage of radiation received by a dental patient is typically small (around 0.150 mSv for a full mouth series).

Figure 7:
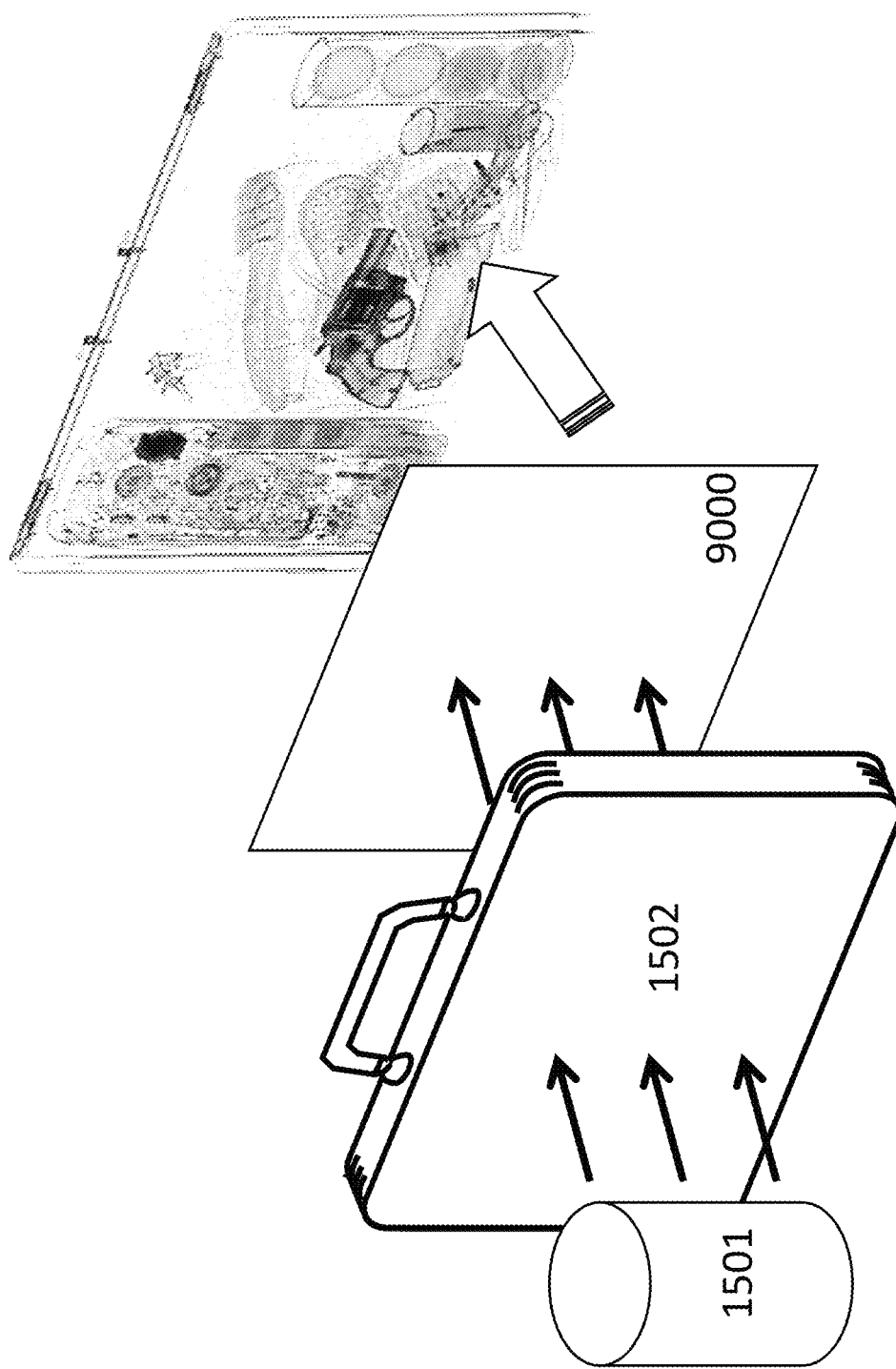

FIG. 7 schematically shows a cargo scanning or non-intrusive inspection (NII) system 9000 comprising the radiation detector 100 as described herein. The system may be used for luggage screening at public transportation stations and airports. The system comprises a radiation source 1501. Radiation emitted from the radiation source 1501 may penetrate a piece of luggage 1502, be differently attenuated by the contents of the luggage, and projected to the system 9000. The system 9000 forms an image by detecting the intensity distribution of the transmitted radiation. The system 9000 may reveal contents of luggage and identify items forbidden on public transportation, such as firearms, narcotics, edged weapons, flammables.

Figure 8:
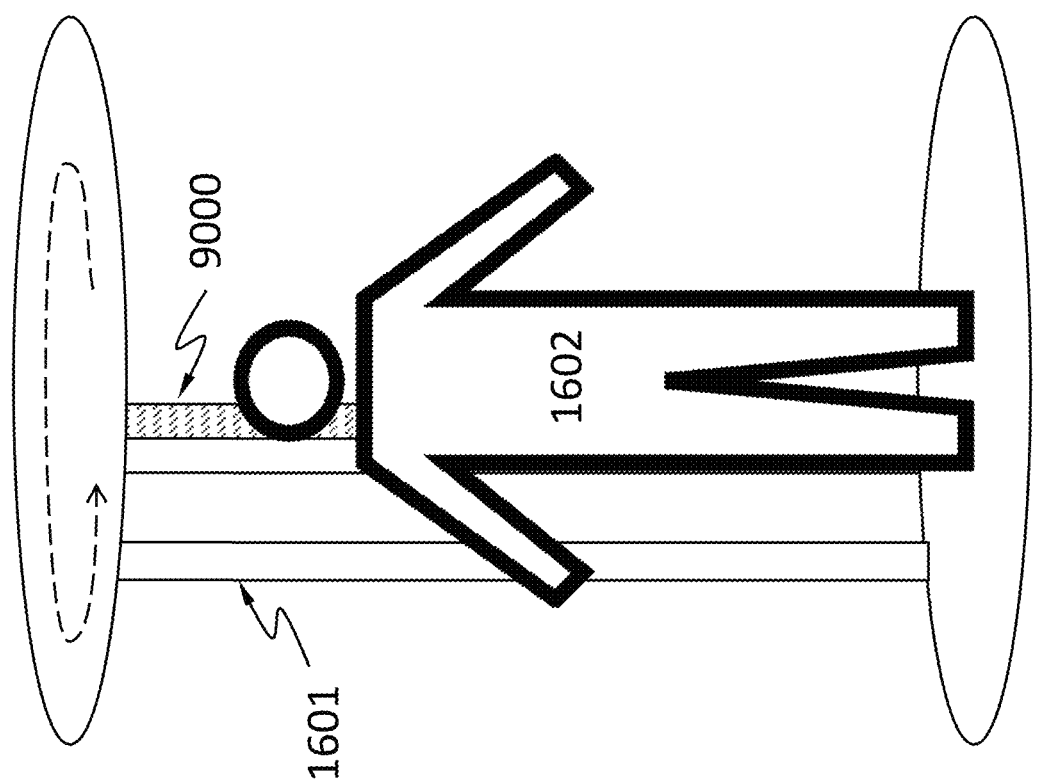

FIG. 8 schematically shows a full-body scanner system 9000 comprising the radiation detector 100 as described herein. The full-body scanner system 9000 may detect objects on a person's body for security screening purposes, without physically removing clothes or making physical contact. The full-body scanner system may be able to detect non-metal objects. The full-body scanner system comprises a radiation source 1601. Radiation emitted from the radiation source 1601 may backscatter from a human 1602 being screened and objects thereon and be projected to the system 9000. The objects and the human body may backscatter radiation differently. The system 9000 forms an image by detecting the intensity distribution of the backscattered radiation. The system 9000 and the radiation source 1601 may be configured to scan the human in a linear or rotational direction.

Figure 9:
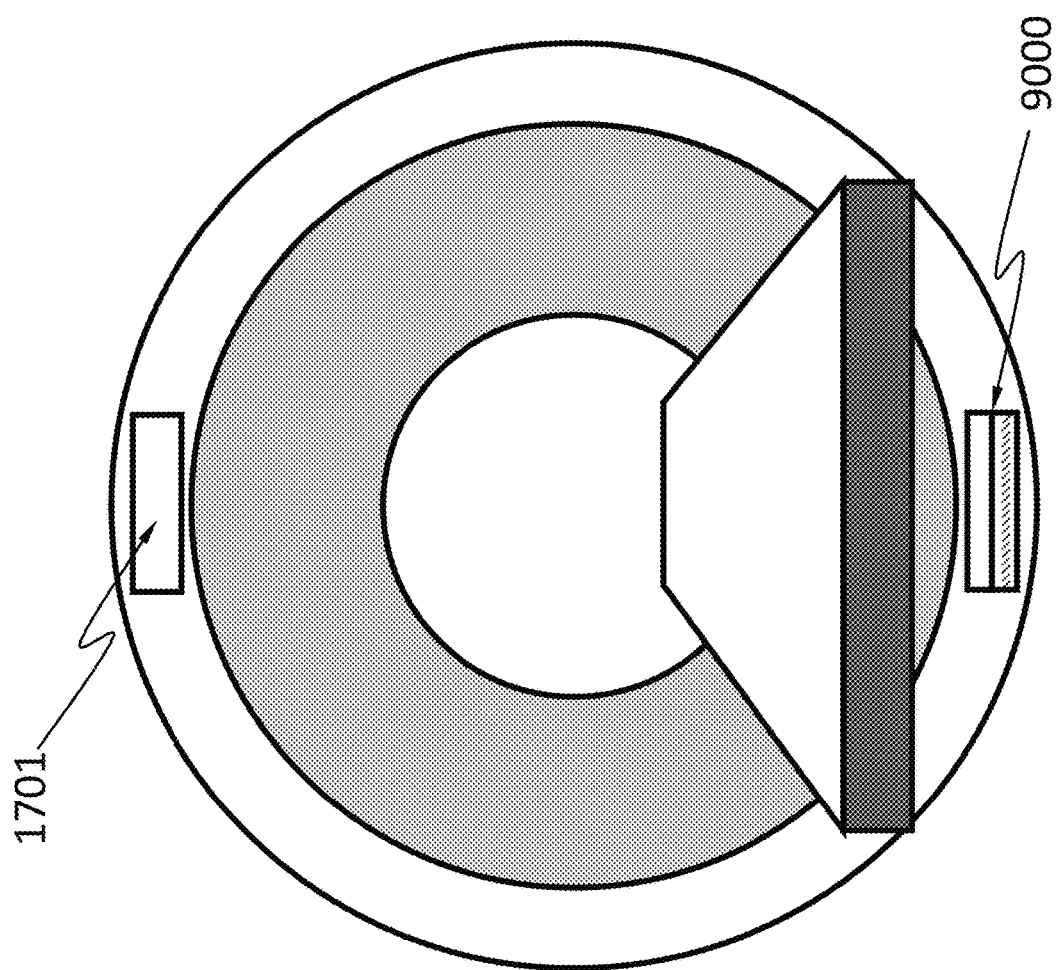

FIG. 9 schematically shows a radiation computed tomography (Radiation CT) system. The Radiation CT system uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The Radiation CT system comprises the radiation detector 100 as described herein and a radiation source 1701. The radiation detectors 100 and the radiation source 1701 may be configured to rotate synchronously along one or more circular or spiral paths.

The radiation detector 100 described here may have other applications such as in a radiation telescope, radiation mammography, industrial radiation defect detection, radiation microscopy or microradiography, radiation casting inspection, radiation non-destructive testing, radiation weld inspection, radiation digital subtraction angiography, etc. It may be suitable to use the system 9000 in place of a photographic plate, a photographic film, a PSP plate, a radiation image intensifier, a scintillator, or another semiconductor radiation detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
an electronics layer comprising a first set of electric contacts and a second set of electric contacts;
a radiation absorption layer configured to absorb radiation;
a first set of electrodes and a second set of electrodes, wherein the first set of electrodes and the second set of electrodes are interdigitated and extend into the radiation absorption layer in a direction of thickness thereof;
wherein the electronics layer and the radiation absorption layer are bonded such that the first set of electrodes are electrically connected to the first set of electric contacts and the second set of electrodes are electrically connected to the second set of electric contacts;
wherein the radiation detector further comprises an insulating layer at a surface of the radiation absorption layer distal from the electronics layer;
wherein the first set of electrodes and the second set of electrodes are attached to the insulating layer.

2. The radiation detector of claim 1, wherein the radiation absorption layer comprises GaAs, CdTe, CZT, or a combination thereof.

3. The radiation detector of claim 1, wherein the first set of electrodes and the second set of electrodes comprise a metal or a semiconductor.

4. The radiation detector of claim 1, wherein the first set of electrodes and the second set of electrodes are configured to be differentially biased.

5. The radiation detector of claim 1, wherein a distance between one of the first set of electrodes to its nearest neighbor of the second set of electrodes does not exceed 2 L, wherein L is the mean free path of charge carriers in the radiation absorption layer.

6. The radiation detector of claim 1, wherein the second set of electrodes are cylindrical in shape.

7. The radiation detector of claim 1, wherein the second set of electrodes are prismatic in shape.

8. The radiation detector of claim 1, wherein the first set of electrodes comprises a grid.

9. The radiation detector of claim 1, wherein the second set of electrodes are discrete.

10. The radiation detector of claim 1, wherein the first set of electrodes and the second set of electrodes are coextensive in the direction of thickness.

11. The radiation detector of claim 1, wherein the radiation absorption layer comprises a polycrystalline semiconductor.

12. The radiation detector of claim 1, wherein the electronics layer is configured to bias the first set of electrodes and the second set of electrodes to different electric voltages through the first set of electric contacts and the second set of electric contacts.

13. The radiation detector of claim 1, wherein the radiation is X-ray.

14. The radiation detector of claim 1,
wherein the electronics layer comprises:
a first voltage comparator configured to compare a voltage of an electric contact of the second set of electric contacts to a first threshold;
a second voltage comparator configured to compare the voltage to a second threshold;
a counter configured to register a number of particles of radiation received by the radiation absorption layer;
a controller, wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, upon determination by the second voltage comparator that an absolute value of the voltage equals or exceeds an absolute value of the second threshold.

15. The radiation detector of claim 14, further comprising an integrator electrically connected to the electric contact, wherein the integrator is configured to collect charge carriers from the electric contact.

16. The radiation detector of claim 14, wherein the controller is configured to activate the second voltage comparator at a beginning or expiration of the time delay.

17. The radiation detector of claim 14, wherein the controller is configured to connect the electric contact to an electrical ground.

18. The radiation detector of claim 14, wherein a rate of change of the voltage is substantially zero at expiration of the time delay.

19. A method comprising:
obtaining a substrate with an insulating layer and a semiconductor layer attached to the insulating layer;
forming a first set of electrodes and a second set of electrodes from the semiconductor layer by etching the semiconductor layer through its entire thickness;
introducing semiconductor particles among the first set of electrodes and the second set of electrodes;
bonding the semiconductor layer with an electronics layer comprising a first set of electric contacts and a second set of electric contacts, such that the first set of electrodes are electrically connected to the first set of electric contacts and the second set of electrodes are electrically connected to the second set of electric contacts.

20. The method of claim 19, wherein the semiconductor particles comprise GaAs, CdTe, CZT, or a combination thereof.

21. The method of claim 19, wherein introducing the semiconductor particles among the first set of electrodes and the second set of electrodes comprises fusing the semiconductor particles.

22. The method of claim 19, wherein the first set of electrodes and the second set of electrodes are configured to be differentially biased.

23. The method of claim 19, wherein a distance between one of the first set of electrodes to its nearest neighbor of the second set of electrodes does not exceed 2 L, wherein L is the mean free path of charge carriers across the semiconductor particles.

24. The method of claim 19, wherein the second set of electrodes are cylindrical in shape.

25. The method of claim 19, wherein the second set of electrodes are prismatic in shape.

26. The method of claim 19, wherein the first set of electrodes comprises a grid.

27. The method of claim 19, wherein the second set of electrodes are discrete.

28. The method of claim 19, wherein the electronics layer is configured to bias the first set of electrodes and the second set of electrodes to different electric voltages through the first set of electric contacts and the second set of electric contacts.

29. The method of claim 19, further comprising removing the insulating layer.

30. A radiation detector, comprising:
an electronics layer comprising a first set of electric contacts and a second set of electric contacts;
a radiation absorption layer configured to absorb radiation;
a first set of electrodes and a second set of electrodes, wherein the first set of electrodes and the second set of electrodes are interdigitated and extend into the radiation absorption layer in a direction of thickness thereof;
wherein the electronics layer and the radiation absorption layer are bonded such that the first set of electrodes are electrically connected to the first set of electric contacts and the second set of electrodes are electrically connected to the second set of electric contacts;
wherein the second set of electrodes are cylindrical in shape or prismatic in shape.

31. The radiation detector of claim 30, wherein the radiation absorption layer comprises GaAs, CdTe, CZT, or a combination thereof.

32. The radiation detector of claim 30, wherein the first set of electrodes and the second set of electrodes comprise a metal or a semiconductor.

33. The radiation detector of claim 30, wherein the first set of electrodes and the second set of electrodes are configured to be differentially biased.

34. The radiation detector of claim 30, wherein a distance between one of the first set of electrodes to its nearest neighbor of the second set of electrodes does not exceed 2 L, wherein L is the mean free path of charge carriers in the radiation absorption layer.

35. The radiation detector of claim 30, wherein the first set of electrodes comprises a grid.

36. The radiation detector of claim 30, wherein the second set of electrodes are discrete.

37. The radiation detector of claim 30, wherein the first set of electrodes and the second set of electrodes are coextensive in the direction of thickness.

38. The radiation detector of claim 30, wherein the radiation absorption layer comprises a polycrystalline semiconductor.

39. The radiation detector of claim 30, wherein the electronics layer is configured to bias the first set of electrodes and the second set of electrodes to different electric voltages through the first set of electric contacts and the second set of electric contacts.

40. The radiation detector of claim 30, wherein the radiation is X-ray.

41. The radiation detector of claim 30,
wherein the electronics layer comprises:
a first voltage comparator configured to compare a voltage of an electric contact of the second set of electric contacts to a first threshold;
a second voltage comparator configured to compare the voltage to a second threshold;
a counter configured to register a number of particles of radiation received by the radiation absorption layer;
a controller, wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, upon determination by the second voltage comparator that an absolute value of the voltage equals or exceeds an absolute value of the second threshold.

42. The radiation detector of claim 41, further comprising an integrator electrically connected to the electric contact, wherein the integrator is configured to collect charge carriers from the electric contact.

43. The radiation detector of claim 41, wherein the controller is configured to activate the second voltage comparator at a beginning or expiration of the time delay.

44. The radiation detector of claim 41, wherein the controller is configured to connect the electric contact to an electrical ground.

45. The radiation detector of claim 41, wherein a rate of change of the voltage is substantially zero at expiration of the time delay.

* * * * *